United States Patent
Johnson et al.

(10) Patent No.: US 7,289,841 B2
(45) Date of Patent: Oct. 30, 2007

(54) METHOD AND APPARATUS FOR VOLUMETRIC CARDIAC COMPUTED TOMOGRAPHY IMAGING

(75) Inventors: Peter C. Johnson, South Euclid, OH (US); Shalabh Chandra, Twinsburg, OH (US); Uri Shreter, Beachwood, OH (US); Ammon Steinberg, Zichron Yacov (IL); Dominic J. Heuscher, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 877 days.

(21) Appl. No.: 10/280,919

(22) Filed: Oct. 25, 2002

(65) Prior Publication Data

US 2004/0082846 A1    Apr. 29, 2004

(51) Int. Cl.
A61B 6/00    (2006.01)
(52) U.S. Cl. .................. 600/431; 600/407; 600/420
(58) Field of Classification Search ................ 600/413, 600/428
See application file for complete search history.

(56) References Cited

U.S. PATENT DOCUMENTS

| | | | | |
|---|---|---|---|---|
| 3,548,807 | A | 12/1970 | Crovella | 128/2.06 |
| 5,273,040 | A | 12/1993 | Apicella et al. | 128/653.2 |
| 5,383,231 | A | 1/1995 | Yamagishi | 378/15 |
| 5,459,769 | A * | 10/1995 | Brown | 378/4 |
| 5,503,149 | A | 4/1996 | Beavin | 128/653.1 |
| 5,903,664 | A * | 5/1999 | Hartley et al. | 382/154 |
| 6,047,080 | A | 4/2000 | Chen et al. | 382/128 |
| 6,081,267 | A * | 6/2000 | Stockham et al. | 715/788 |
| 6,154,516 | A * | 11/2000 | Heuscher et al. | 378/15 |
| 6,260,021 | B1 * | 7/2001 | Wong et al. | 705/2 |
| 7,006,862 | B2 * | 2/2006 | Kaufman et al. | 600/523 |
| 2003/0171671 | A1 * | 9/2003 | Miyazaki | 600/420 |

FOREIGN PATENT DOCUMENTS

| | | |
|---|---|---|
| EP | 0 953 942 A2 | 11/1999 |
| EP | 0 983 747 A1 | 3/2000 |
| WO | WO 01/45047 A1 | 6/2001 |

OTHER PUBLICATIONS

Sandstede et al. Optimization of automatic bolus tracking for timing of the arterial phase of helical liver CT .Eur. Radiol. (2001) 11: 1396±1400.*

Achenbach, et al. "Noninvasive Coronary Angiography By Retrospectively ECG-Gated Multislice Spiral CT", Circulation Dec. 5, 2000, US, vol. 102, No. 23, pp. 2823-2828, XP002266285.

* cited by examiner

Primary Examiner—Eleni Mantis Mercader
Assistant Examiner—Ashish Jasani

(57) ABSTRACT

In a diagnostic cardiac imaging session of a patient's heart using a computed tomography imaging scanner (10) and a cardiac cycle monitor (42), a diagnostic objective (100) is received. Survey imaging (104) of the heart is performed to determine optimized imaging parameter values for the received diagnostic objective (100). Monitor imaging (108) of a limited portion of the heart is performed during influx of a contrast agent (22) using a low patient x-ray exposure condition to detect a trigger condition. Volume imaging (110) of the heart responsive to detection of the trigger condition is performed using the optimized imaging parameter values to obtain volumetric imaging data. Cardiac cycle data is recorded during at least a portion of the survey imaging (104), the monitor imaging (108), and the volume imaging (110). High resolution reconstructing (130) of at least some volumetric imaging data is performed to produce high resolution image representations (132).

28 Claims, 12 Drawing Sheets

METHOD AND APPARATUS FOR VOLUMETRIC CARDIAC COMPUTED TOMOGRAPHY IMAGING

BACKGROUND OF THE INVENTION

The present invention relates to the medical imaging arts. It particularly relates to helical or multi-slice volumetric cardiac computed tomography (CT) imaging, and will be described with particular reference thereto. However, the invention will also find application in the computed tomographic imaging of other dynamically moving organs, in angiographic imaging, and in medical imaging of dynamically moving organs using other medical imaging techniques such as magnetic resonance imaging (MRI) and nuclear medical imaging.

Cardiac volumetric computed tomography (CT) imaging typically employs an x-ray source that generates a fan-beam, wedge-beam, or cone-beam of x-rays that traverse an examination region within which a patient's heart is disposed. The cardiac tissue, coronary arteries, and blood therewithin interacts with and absorbs a portion of the traversing x-rays. Typically, a contrast agent is administered to the patient to improve blood contrast. A one- or two-dimensional radiation detector arranged opposite the x-ray source detects and measures intensities of the transmitted x-rays.

During scanning the patient is linearly advanced between axial scans to perform multi-slice CT imaging, or the patient is continuously linearly advanced during x-ray source rotation to perform helical CT imaging. The imaging data is reconstructed using a filtered backprojection, a PI reconstruction, or the like to generate volumetric image representations. Preferably, the cardiac cycle is monitored by an electrocardiograph or other device, and the imaging data is binned into cardiac phase bins to reconstruct the heart at a plurality of phases.

A wide range of cardiac studies are performed using cardiac CT. Qualitative review of cardiac CT images by trained medical personnel detects congenital heart defects, large aneurysms or stenoses in the major coronary arteries, and other gross anatomical abnormalities. Analyses such as heart pumping capacity measurements, blood perfusion studies in myocardium, and coronary vessel tracking provide complementary quantitative diagnostic information.

Modern multi-slice and helical CT scanners produce large quantities of data. In a typical cardiac imaging session, a portion of the heart extending about 12 cm along the head-to-foot direction is imaged using approximately 180 axial slices to provide high spatial resolution. The cardiac cycle is typically binned into about 10 cardiac phase bins to provide good temporal resolution, so that 1800 slices are acquired in the cardiac imaging session.

Reconstruction of this plethora of data is time consuming. Moreover, for certain cardiac diagnostic objectives, not all the imaging data is necessary. For qualitative study of congenital heart defects or other gross anatomical features, image reconstructions at only one or two optimal cardiac phases is often sufficient. Similarly, coronary vessel tracking is preferably performed on an image reconstruction at a selected optimal cardiac phase in which the tracked coronary artery is substantially stationary.

Although for certain studies only one or a few optimal cardiac phases are needed, typically all the CT imaging data is reconstructed, and then the optimal cardiac phases are identified from the complete set of reconstructed images. Additionally, for other diagnostic objectives such as ventricular functional analysis, the complete set of reconstructed images is used.

Present CT imaging systems typically include a CT scanner and associated data acquisition and image reconstruction software, which produces a complete set of reconstructed images. The operator performs initial planar survey scans to identify a spatial position of the heart and to optimize other imaging parameters. The contrast agent is then administered, and low-dosage imaging is performed to monitor the contrast agent intake into the heart. When the image contrast due to contrast agent reaches a selected threshold, the operator initiates high resolution diagnostic imaging. Typically, the operator is given little guidance on optimizing the survey, monitoring, and diagnostic imaging steps. Once the diagnostic imaging is complete, the full CT data set is reconstructed.

Once the data is collected and reconstructed, a suitable analysis module is selected from a suite of analysis software modules. Each module in the analysis software suite is independently designed and configured for a specific diagnostic objective. There is typically no communication between the analysis modules, or between the analysis software suite and the data acquisition and reconstruction software components.

This disconnected modular arrangement has a number of disadvantages. Because the modules are substantially separate, common processing elements such as selection of optimal cardiac phases are duplicated.

The disconnected nature of the arrangement provides little guidance to the user in planning and coordinating the cardiac CT imaging session. A significant amount of time and effort is expended in selecting and initiating each step of the session workflow. Because a contrast agent is typically employed in cardiac CT imaging, coordinated timing of the imaging session with the contrast agent intake is important to ensure that contrast-enhanced images comporting with the specific diagnostic objective or objectives are obtained.

For diagnostic objectives where only one or a few cardiac phases are optimally selected, the disconnect between the data acquisition and reconstruction software components and the analyses software suite means that the complete set of images is reconstructed prior to selection of the optimal cardiac phases. This results in substantial unnecessary reconstruction processing.

The present invention contemplates an improved apparatus and method that overcomes the aforementioned limitations and others.

SUMMARY OF THE INVENTION

According to one aspect of the invention, an apparatus is disclosed for performing a diagnostic cardiac imaging session of a patient's heart. A survey imaging means is provided for survey imaging the heart to determine optimized imaging parameter values for a received diagnostic objective. A monitor imaging means is provided for monitor imaging a limited portion of the heart during influx of a contrast agent using a low patient x-ray exposure condition to detect a trigger condition. A volume imaging means is provided for volume imaging the heart responsive to detection of the trigger condition using the optimized imaging parameter values to obtain volumetric imaging data. A cardiac cycle recording means is provided for recording cardiac cycle data during at least a portion of the survey imaging, the monitor imaging, and the volume imaging. A volumetric reconstructing means is provided for high resolution reconstructing at least a portion of the volumetric imaging data to produce high resolution image representations of at least a portion of the heart.

According to another aspect of the invention, a method is provided for performing a diagnostic cardiac imaging session of a patient's heart using a computed tomography imaging scanner and a cardiac cycle monitor. Survey imaging of the heart is performed to determine optimized imaging parameter values for a received diagnostic objective. Monitor imaging of a limited portion of the heart is performed during influx of a contrast agent using a low patient x-ray exposure condition to detect a trigger condition. Volume imaging of the heart is performed responsive to detection of the trigger condition using the optimized imaging parameter values to obtain volumetric imaging data. Cardiac cycle data is recorded during at least a portion of the survey imaging, the monitor imaging, and the volume imaging. Volumetric reconstructing of at least a portion of the volumetric imaging data is performed to produce high resolution image representations of at least a portion of the heart.

According to yet another aspect of the invention, a cardiac computed tomography imaging apparatus is disclosed for performing a diagnostic cardiac imaging session. A computed tomography imaging scanner acquires imaging data of a patient's heart. An electrocardiograph acquires electrocardiographic data to monitor a cardiac phase of the patient's heart. An imaging controller communicates with the imaging scanner and the electrocardiograph to coordinate the diagnostic cardiac imaging session. The imaging controller performs an imaging session method including: survey imaging the heart to determine optimized imaging parameter values for a received diagnostic objective; monitor imaging a limited portion of the heart during influx of a contrast agent using a low patient x-ray exposure condition to detect a trigger condition; volume imaging the heart responsive to detection of the trigger condition using the optimized imaging parameter values to obtain volumetric imaging data; recording electrocardiographic data during at least a portion of the survey imaging, the monitor imaging, and the volume imaging; and high resolution reconstructing at least a portion of the volumetric imaging data to produce high resolution image representations of at least a portion of the heart.

One advantage of the present invention resides in a comprehensive cardiac CT imaging workflow that provides substantial guidance to the user in performing cardiac CT imaging with a specific diagnostic objective.

Another advantage of the present invention resides in reduced image reconstruction processing for a diagnostic objective which utilizes a sub-set of the complete cardiac CT imaging data set.

Yet another advantage of the present invention resides in streamlining a cardiac CT imaging session by integrating the data acquisition, image reconstruction, cardiac image review, and quantitative analysis steps.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
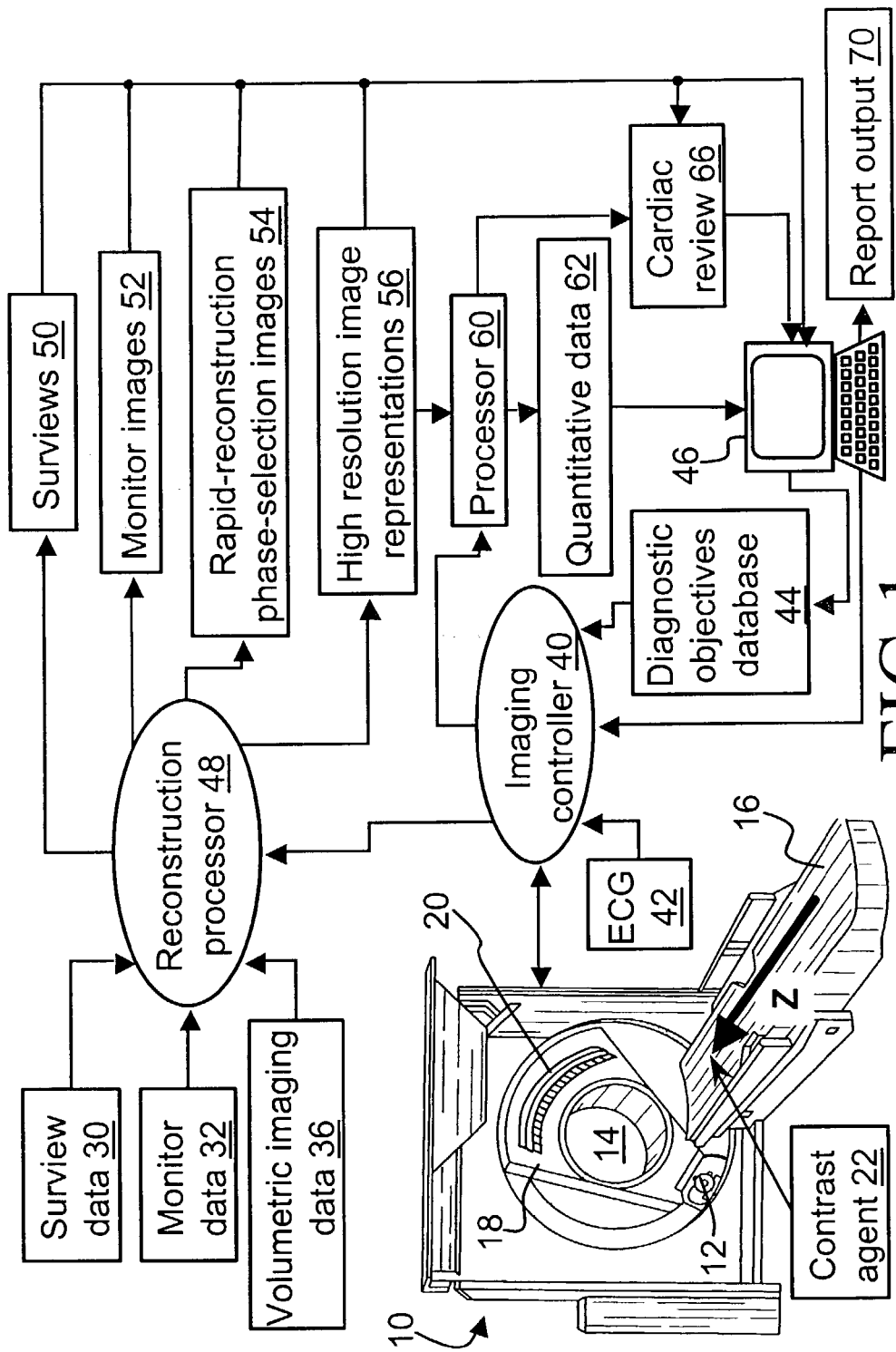
FIG. 1 shows an exemplary cardiac computed tomography imaging apparatus which includes an integrated cardiac CT imaging session workflow.

With reference to FIG. 1, a computed tomography (CT) imaging scanner 10 includes an x-ray source 12 that produces a fan-shaped, cone-shaped, wedge-shaped, or otherwise-shaped x-ray beam directed into an examination region 14 which contains a patient arranged on a patient support 16 with the patient's heart substantially centered within the examination region 14. The patient support 16 is linearly movable in a Z-direction while the x-ray source 12 is mounted on a rotating gantry 18 that rotates around the Z-axis.

In a helical CT imaging mode, the rotating gantry 18 rotates simultaneously with linear advancement of the patient support 16 to produce a generally helical trajectory of the x-ray source 12 about the examination region 14. For helical CT imaging, the x-ray source 12 preferably produces a cone-shaped x-ray beam that diverges in the Z-direction.

In a multi-slice imaging mode, the rotating gantry 18 rotates while the patient support 16 remains stationary to produce a generally circular trajectory of the x-ray source 12 about the examination region 14 during which an axial slice image is acquired. The patient support 16 is then stepped a pre-determined distance in the Z-direction and the axial slice image acquisition is repeated in iterative fashion to acquire volumetric imaging data in discrete steps along the Z-direction. For multi-slice CT imaging, the x-ray source 12 preferably produces a fan-shaped or wedge-shaped x-ray beam with limited divergence in the Z-direction.

An x-ray detector 20 is arranged on the gantry 18 across from the x-ray source 12. In the exemplary CT scanner 10, the x-ray detector 20 spans a selected angular range that preferably comports with a fan angle of the x-ray beam. The x-ray detector 20 preferably includes several rows of detectors along the Z-direction for simultaneously acquiring imaging data along a portion of the Z-direction in each projection view. The span of the detector rows in the Z-direction preferably comports with a divergence or width of the x-ray beam in the Z-direction. The x-ray detector 20 is arranged on the rotating gantry 18 opposite to the x-ray source 12 and rotates therewith so that the x-ray detector 20 receives x-rays that traverse the examination region 14 as the rotating gantry 18 rotates.

Instead of the arrangement of the detector 20 shown in FIG. 1, it is also contemplated to arrange the x-ray detector on a stationary gantry encircling the rotating gantry such that the x-rays continuously impinge upon a continuously shifting angular portion of the radiation detector during x-ray source rotation.

In cardiac CT imaging, a contrast agent 22 that selectively improves x-ray contrast of the blood is typically administered. The contrast agent 22 is typically a fluid which is administered as an intravenous drip at a steady state rate to provide a generally steady state x-ray contrast for cardiac CT imaging. For perfusion studies or contrast intake studies, a bolus injection of the contrast agent 22 is administered, in which a large quantity of the fluid is rapidly intravenously injected.

With continuing reference to FIG. 1, the gantry 18 and the patient support 16 cooperate to obtain selected projection views of the subject along a helical or circular trajectory of the x-ray source 12 about the examination region 14. The trajectory of the x-ray source 12 during acquisition of the projection views preferably provides substantial angular coverage for each voxel of the imaged region of interest to reduce image artifacts. Projection data collected by the x-ray detector 20 are communicated to one of several data acquisition memories depending upon the portion of the cardiac CT imaging session being performed.

In particular, a survey view (i.e., "surview") data memory 30 stores images initially acquired during patient setup. The survey views typically include non-rotating anterior-posterior and optional lateral views, although other types of survey views can be acquired. The limited angular coverage of the survey views beneficially produces limited patient x-ray exposure during the surviews.

A monitor data memory 32 stores images acquired while waiting for intake of the administered contrast agent 22 into the cardiac region. Typically, the monitor imaging data corresponds to a non-rotating view or a single axial view acquired using a low x-ray dosage to minimize patent x-ray exposure during the monitoring. An image intensity of a selected image portion corresponding to the cardiac region, such as an aortic image region, is monitored to estimate a density of contrast agent in the selected region. A trigger condition defined as a characteristic of the density-time curve for the aortic image portion or other selected image portion is detected to initiate diagnostic cardiac imaging.

A volumetric imaging data memory 36 stores imaging data acquired for performing the cardiac diagnostic objective. Typically, the diagnostic imaging includes acquiring high resolution helical or multi-slice CT imaging data that spatially spans the cardiac region and that additionally spans at least one period of the cardiac cycle. In a typical cardiac CT imaging session, a 12 cm portion of the heart is imaged using about 180 axial slices to provide spatial resolution in the slice direction. About ten cardiac phases that span a cardiac cycle period are acquired. Hence the cardiac CT imaging session includes acquiring about 1800 axial slices.

The survey imaging, monitor imaging, and diagnostic volumetric CT imaging are coordinated by an imaging controller 40. A cardiac cycle monitor which is typically an electrocardiograph (ECG) 42 monitors the cardiac cycle. A user communicates with the imaging controller 40 and with a diagnostic objectives database 44 via a graphical user interface 46 to select one of a plurality of stored cardiac CT imaging sessions. The selected imaging session tailors the survey imaging, the monitoring imaging, and the diagnostic imaging to acquire imaging data from which the diagnostic objective or objectives are readily achieved. Moreover, the selected imaging session accesses and tailors qualitative and/or quantitative analyses to efficiently accomplish the diagnostic objective or objectives.

A reconstruction processor 48 reconstructs the acquired projection data, using filtered backprojection, an n-PI reconstruction method, or other reconstruction method, to generate image representations of the subject or of a selected portion thereof. A surviews image memory 50 and a monitor images memory 52 corresponding to the surviews imaging data memory 30 and the monitor imaging data memory 32, respectively, store the reconstructed surviews and monitor images, respectively.

The volumetric imaging data 36 stores a large quantity of imaging data, corresponding to about 1800 high resolution slices for the exemplary imaging session. The reconstruction of this imaging data is performed to produce image representations comporting with the diagnostic objectives selected from the database 44. For example, if the selected diagnostic objective is suitably accomplished using one cardiac phase or a limited sub-set of the acquired cardiac phases, the imaging controller 40 preferably performs a rapid reconstruction of the data using a low voxel resolution, a limited number of slices, or the like, to generate cardiac phase selection images that are stored in a phase selection images memory 54. One or more optimal cardiac phases are selected automatically, e.g. based upon cardiac motion analysis of the phase selection images, or manually by the user via the graphical user interface 46.

Volumetric imaging data from the memory 36 corresponding to the selected one or more phases is reconstructed by the reconstruction processor 48 and resultant high resolution image representations are stored in a high resolution image representations memory 56. For certain types of diagnostic objectives, such as ventricular functional analysis, the complete volumetric imaging data set stored in the memory 36 is employed in the analysis. In these cases the full imaging data set stored in the volumetric imaging data memory 36 is reconstructed and stored in the high resolution image representations memory 56.

Preferably, each reconstructed image in the image representations memory is associated with cardiac phase information determined from electrocardiographic data acquired by the electrocardiograph 42 during the imaging. Optionally, images in the surviews memory 50 and/or the monitor images memory 52 are also associated with cardiac phase information.

With continuing reference to FIG. 1, the high resolution images stored in the memory 56 are processed by a processor 60 under the coordination of the imaging controller 40 based upon the cardiac CT imaging session selected by the user from the diagnostic objectives database 44. The processor 60 performs a selected one or more quantitative analyses, such as coronary artery tracking and analysis, ventricular functional analysis, coronary delivery analysis, or the like as called for by the selected cardiac CT imaging session. Quantitative results produced by these analyses are stored in a quantitative data memory 62 which is accessible by the user via the graphical user interface 46.

If the diagnostic session selected by the user from the diagnostic objectives database 44 calls for a qualitative visual review of the acquired high resolution cardiac image representations by a medically skilled user, the processor 60 invokes a cardiac review processor 66, which produces three-dimensional renderings of the high resolution image representations stored in the memory 56, CINE animations thereof, extracts selected slices such as coronal, sagittal, axial, or oblique slices, generates maximum intensity projections (MIP's), or otherwise produces visual representations of the imaging data which are displayed to the user on the graphical user interface 46. The cardiac review processor 66 is also suitably invoked by the processor 60 for providing the user with images for selection of regions of interest on which quantitative analyses are to be performed.

After the qualitative and quantitative studies are performed, a report output 70 is generated. Preferably, the report is generated based upon a report form corresponding to the selected imaging session and stored in the diagnostic objectives database 44. The quantitative data stored in the memory 62, exemplary cardiac images selected by the user via the cardiac review 66, along with user-input comments are integrated into the report form to generate the report output 70.

The cardiac CT imaging system described with reference to FIG. 1 is exemplary only. Those skilled in the art can readily modify or add to the illustrated system to suit specific applications. For example, the various data memories 30, 32, 36, image memories 50, 52, 54, 56, the diagnostic objectives database 44, and quantitative data memory 62 are shown as separate memories but can also be integrated in various ways on one or more data storage devices such as a data storage unit of a hospital information network, a hard drive of the graphical user interface 46, or the like.

The reconstruction processor 48, the imaging controller 40, the processor 60, the cardiac review processor 66, and the graphical user interface 46 can similarly be integrated in various ways, as for example: a single computer; a plurality of interconnected computers; a computer-based user interface 46, cardiac review processor 66, and processor 60 in combination with dedicated hardware for the reconstruction processor 48, and the imaging controller 40; or other arrangements. The graphical user interface 46 is optionally interfaced with a communication network such as a hospital or clinic information network via which image reconstructions are transmitted to medical personnel, a patient information database is accessed, or the like. Similarly, the graphical user interface 46 is optionally connected with the Internet.

Figure 2:
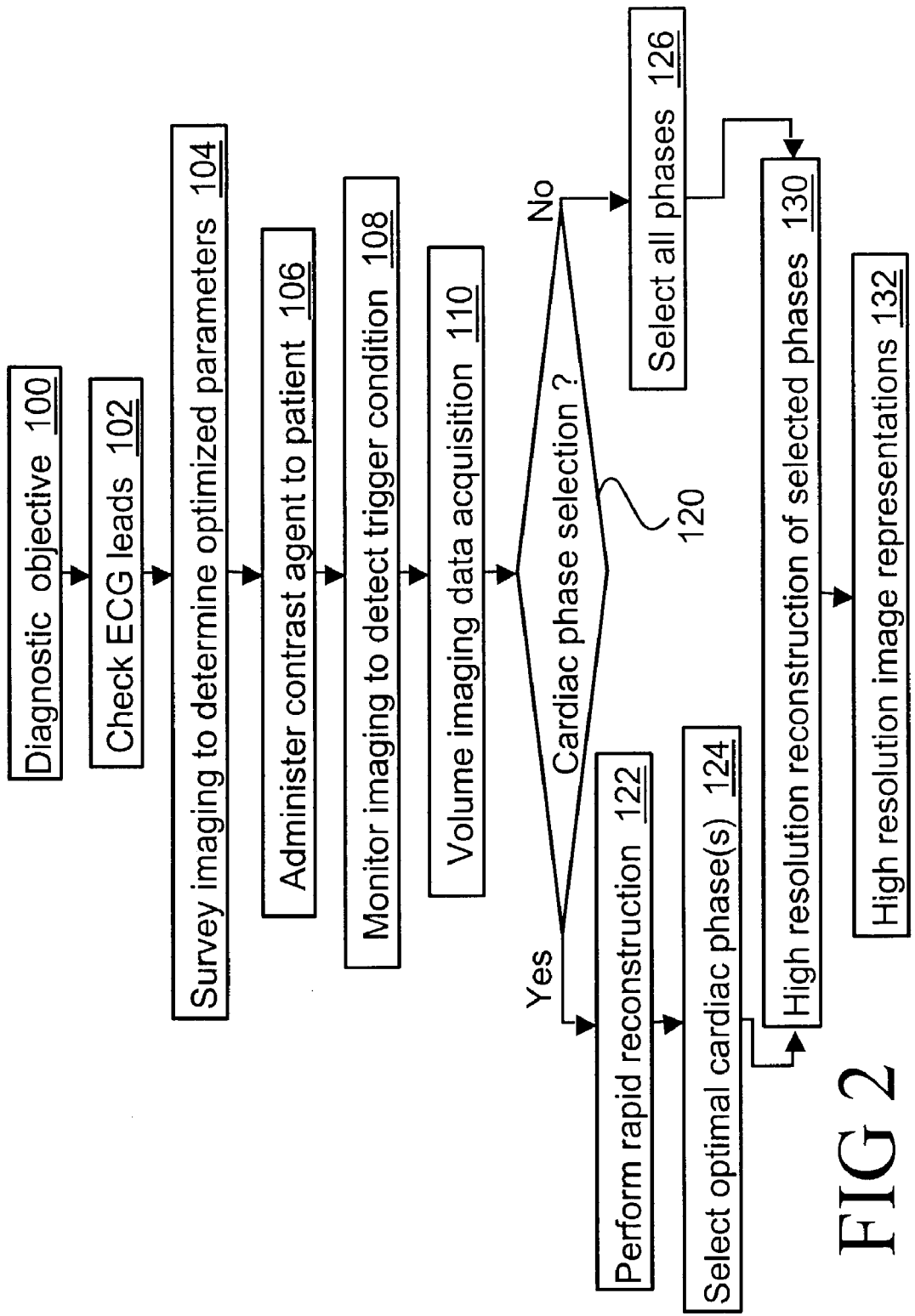
FIG. 2 shows a portion of a preferred integrated cardiac CT imaging session workflow, from selection of a diagnostic objective through high resolution image reconstruction of one, a few, or all acquired cardiac phases.

With continuing reference to FIG. 1 and with further reference to FIG. 2, a suitable cardiac CT image data acquisition session implemented by the cardiac CT imaging system of FIG. 1 is described. At least one diagnostic objective 100 is selected from the diagnostic objectives database 44. Selection of the diagnostic objective 100 also selects a corresponding imaging session program stored in the database 44 for implementation under the control of the imaging controller 40.

The electrocardiograph leads are checked in a step 102. Preferably, the imaging controller 40 automatically checks the electrocardiographic signal. If the signal is abnormal, the faulty lead is identified and the user is notified that correction should be made. Optionally, if the number of electrocardiographic leads connected to the patient is greater than a number of leads needed for monitoring the cardiac cycling, the imaging controller 40 responds to a faulty lead by switching to another lead that is performing normally.

Once a suitable electrocardiographic signal is established, survey imaging is performed in a step 104 to determine optimized imaging parameters for the selected cardiac CT session. Such parameters preferably include defining a region of interest typically including the heart or a portion thereof, and identifying an optimal helical pitch (for helical CT) or step size and time interval for linear advancement of the patient support 16 (for multi-slice CT). The helical pitch or patient support parameters are suitably computed based on a cardiac cycle period which is determined from the electrocardiographic signal, and a size or length along the Z-direction of the region of interest. Of course, other imaging parameters such as an intensity of the x-ray source 12, patient positioning on the patient support 16, and so forth are also suitably optimized using surviews of the step 104.

With continuing reference to FIGS. 1 and 2, the contrast agent 22 is administered to the patient in a step 106. The contrast agent can be administered as a continuous steady state intravenous drip for steady state imaging, or as a rapid bolus injection for blood perfusion studies or the like. Preferably, the selected imaging session program provides prompts to the user indicating when the contrast agent 22 should be administered, and in what form (e.g., intravenous drip or bolus injection).

The patient is then monitored using the CT apparatus 10 in a step 108 to monitor intake of the contrast agent 22 into the cardiac region, and to detect a trigger condition. Preferably, a selected monitor region such as a portion of the aorta is monitored by repetitive CT imaging to determine a density of the monitored region. The trigger condition is a selected characteristic of a density-time plot for the selected monitor region.

Volumetric cardiac CT imaging is initiated in a step 110 responsive to a detected occurrence of the trigger condition. The volumetric imaging is performed using the optimized parameters obtained in the survey imaging step 104 and other settings included in the cardiac imaging session program. The imaging typically includes acquiring a large number of axial slices spanning the region of interest such as the heart, and further spans at least one cardiac cycle period. Typically, over one thousand axial slices are acquired in the volumetric imaging step 110, and the volumetric imaging data are stored in the volumetric imaging data memory 36.

In a decision step 120, the imaging controller 40 makes a decision as to whether to reconstruct the full set of volumetric imaging data, or only a selected portion thereof. This decision is made based on the diagnostic objective 100. For certain diagnostic objectives such as coronary artery analysis, high resolution images at one or a few cardiac phases may be sufficient to perform the diagnostic task.

If a sub-set of the available cardiac phases is to be reconstructed at high resolution, then a rapid reconstruction of the set of volumetric imaging data spanning the cardiac cycle period is performed. Rapid reconstruction is achieved by reconstructing at a low voxel resolution, or by reconstructing only selected representative cardiac phases or slices. One or more optimal cardiac phases are selected in a step 124, either using manual selection or an automated selection based on anatomical motion or other characteristics of the rapidly reconstructed images.

If the diagnostic objective 100 calls for using the full set of volumetric imaging data stored in the memory 36, then all cardiac phases are selected in a step 126. Once one, a few, or all cardiac phases are selected for reconstruction according to the steps 120, 122, 124, 126, imaging data corresponding to the selected cardiac phases are reconstructed at high resolution in a step 130 to produce high resolution image representations 132.

Figure 3:
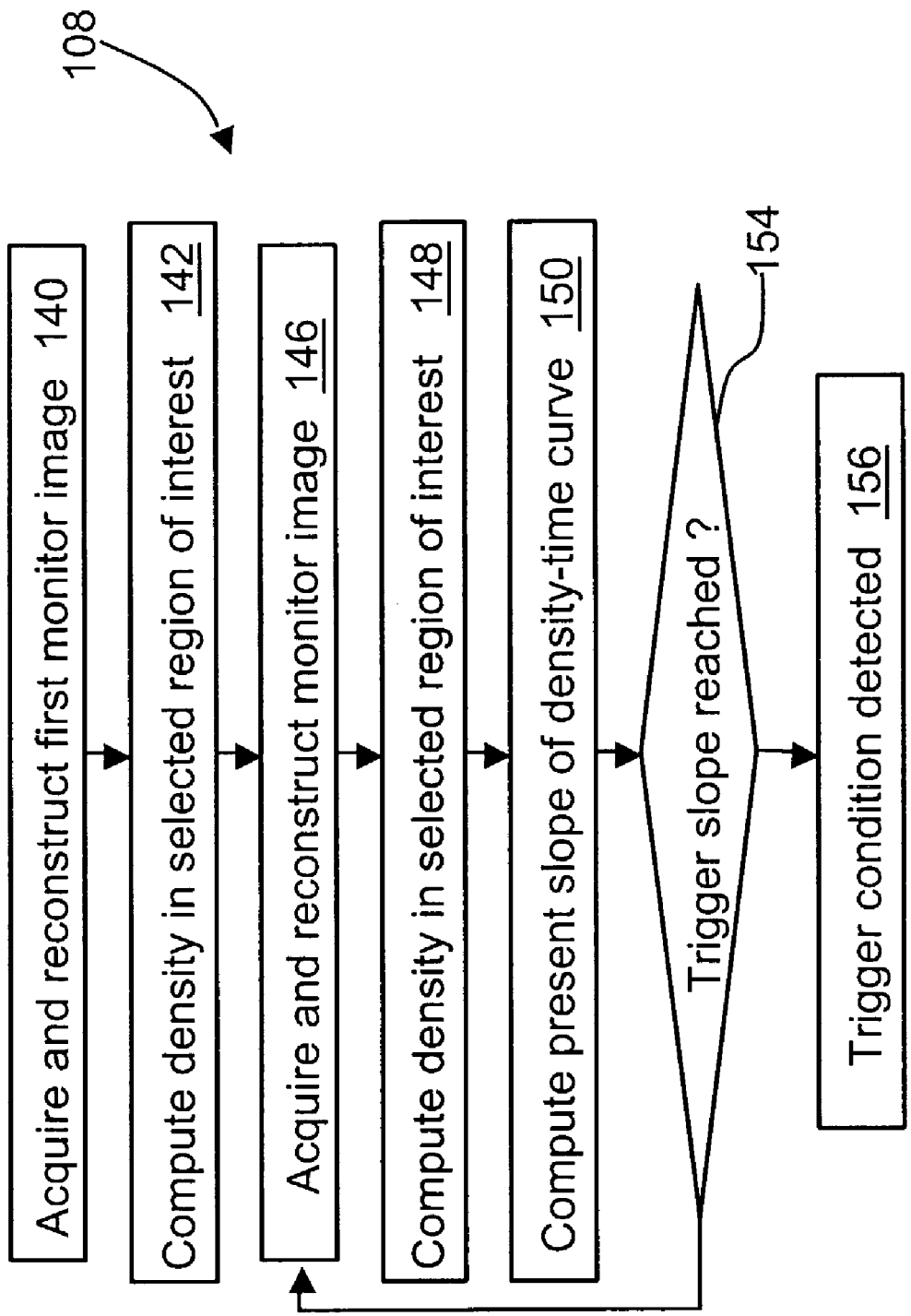
FIG. 3 shows a preferred method for detecting an optimal time to initiate the high resolution volumetric cardiac imaging.

With continuing reference to FIGS. 1 and 2 and with further reference to FIG. 3, a preferred method for performing the monitoring step 108 to detect the trigger condition for initiating volumetric CT imaging is described. In a step 140, a first monitor image is acquired and reconstructed. The monitor image is preferably acquired using a low x-ray intensity to limit radiation exposure to the patient. The acquired data is stored in the monitor data memory 32, reconstructed by the reconstruction processor 48, and the reconstructed image is stored in the monitor images memory 52. Based on the monitor image, a first density parameter for a monitor region of the first monitor image such as a selected portion of the aorta or other large blood vessel computed in a step 142 based on intensities of voxels corresponding to the monitor region.

In steps 146, 148 a second monitor image is acquired and a density computation is performed for the second monitor image. The first and second monitor images are acquired in the steps 140, 146 which are temporally separated by a time interval, and so the density values for the first and second monitor images form a beginning of a density-time curve. In a step 150, a slope of the density-time curve is computed, and the computed slope is compared with a selected trigger slope in a decision step 154. If the present slope of the density-time curve is less than the trigger slope, the acquisition and density computation steps 146, 148 are repeated to tracking the density-time curve, and the steps 146, 148 are repeated until the present slope reaches the trigger slope, thus detecting the trigger condition in a step 156.

Although the method shown in FIG. 3 is preferred, those skilled in the art can readily monitor and detect other characteristics of the density-time curve, such as detecting a threshold density as the trigger condition. However, triggering based on a slope of the density-time curve rather than a threshold trigger advantageously reduces dependence of the triggering on the absolute voxel intensity which can vary from patient to patient.

Figure 4:
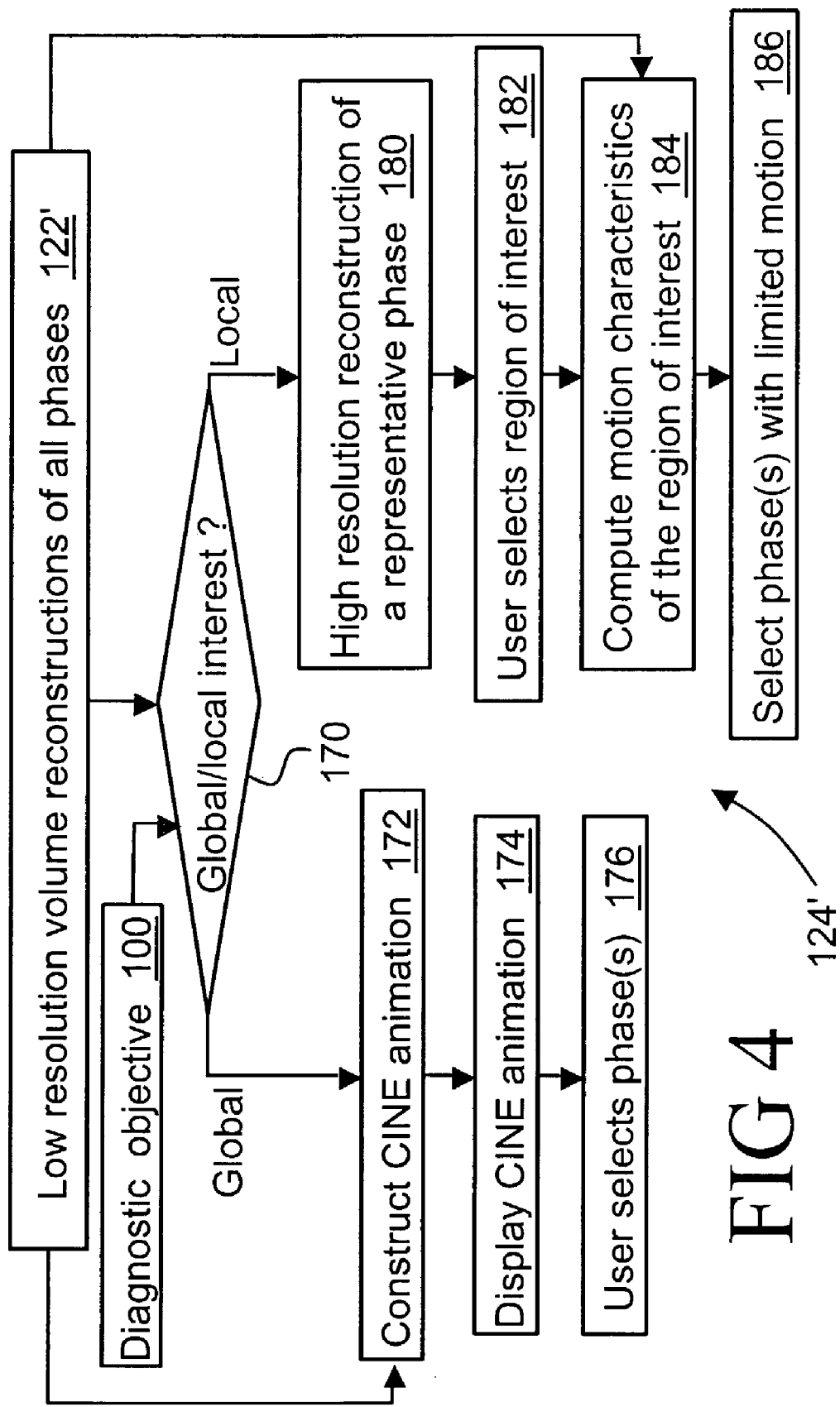
FIG. 4 shows one preferred embodiment for selecting optimal cardiac phases for a specific diagnostic objective as part of the preferred cardiac CT imaging session workflow.

With continuing reference to FIGS. 1 and 2 and with further reference to FIG. 4, a first preferred method for selecting a sub-set of the cardiac phases for high resolution reconstruction is described. The rapid reconstruction step 122 performs a low resolution reconstruction of all cardiac CT data stored in the memory 36 including all cardiac phases in a step 122', and the low resolution images are stored in the rapid reconstruction phase-selection images memory 54.

For example, if a high resolution reconstruction employs a square reconstruction grid having 256 voxels on a side, the low resolution reconstruction is performed at a lower voxel resolution such as at 128 voxels on a side. That is, the linear voxel dimension of each slice is reduced by one-half, corresponding to a factor of four reduction in the number of voxels per slice. Optionally, for volumetric rapid reconstruction only a portion of the slices are reconstructed, e.g. every other slice along the Z-direction. The factor of four reduction in slice resolution coupled with omitting every other slice along the Z-direction results in a rapid reconstruction with one-eighth the number of voxels of a high resolution reconstruction. Of course, other decreases in resolution such as using a 64×64 voxel slice grid can also be employed, with those skilled in the art making a suitable trade-off between speed of the rapid reconstruction 122' and image quality for the rapidly reconstructed images.

Based on the low resolution images produced by the rapid reconstruction step 122', one or more optimal cardiac phases are selected in the step 124, and more particularly in a step 124' for the first preferred phase selection method of FIG. 4. A decision step 170 directs the selection process 124' based on whether the selection is made on a global basis or a localized basis. If the diagnostic objective 100 principally includes a global characterization of the heart, e.g. a ventricular functional analysis, then a global selection path is preferably followed because the selected cardiac phases should be optimal over a substantial portion of the heart. However, if the diagnostic objective 100 targets a selected region of interest such as a selected coronary artery, then a local selection path is preferably followed which selects phases which are optimal for the diagnostic objective 100 in the local region of interest.

Considering first the global selection path, a cinematic animation (i.e., CINE animation) is preferably constructed from the low resolution volumetric images in a step 172. The CINE animation is displayed to the user in a step 174, and the user selects the one or more optimal cardiac phases in a step 176. The CINE animation provides the user with an easily comprehended visual representation of cardiac motion, and the user typically selects an optimal cardiac phase or phases in which the overall cardiac motion is limited.

For the local selection path, in addition to the low resolution reconstructions of the step 122' a high resolution reconstruction of one reference cardiac phase is performed in a step 180. The reference cardiac phase is selected substantially randomly, or is selected to approximately correspond with a cardiac phase that is expected to be optimal. It is particularly pointed out that the reference cardiac phase is not necessarily one of the ultimately selected optimal cardiac phases. Rather, the reference high resolution cardiac phase is used for selection of a region of interest.

The high resolution reconstructed reference cardiac phase is displayed to the user for user selection of the local region of interest in a step 182. Alternatively, one of the low resolution cardiac phase reconstructions of the step 122' can be used for the user selection step 182; however, the user may have difficulty identifying the region of interest at the low resolution.

The selected region of interest is tracked across the cardiac phases to compute motion characteristics of the region of interest in a step 184. The step 184 employs edge enhancement, region growing, or another technique along with boundary conditions such as motion limits of the region of interest to identify the region of interest in successive cardiac phase images. By referencing timing information provided by the corresponding electrocardiographic signal, a motion-phase curve is constructed, and one or more optimal cardiac phases in which the region of interest has limited motion are selected in a step 186.

Figure 5:
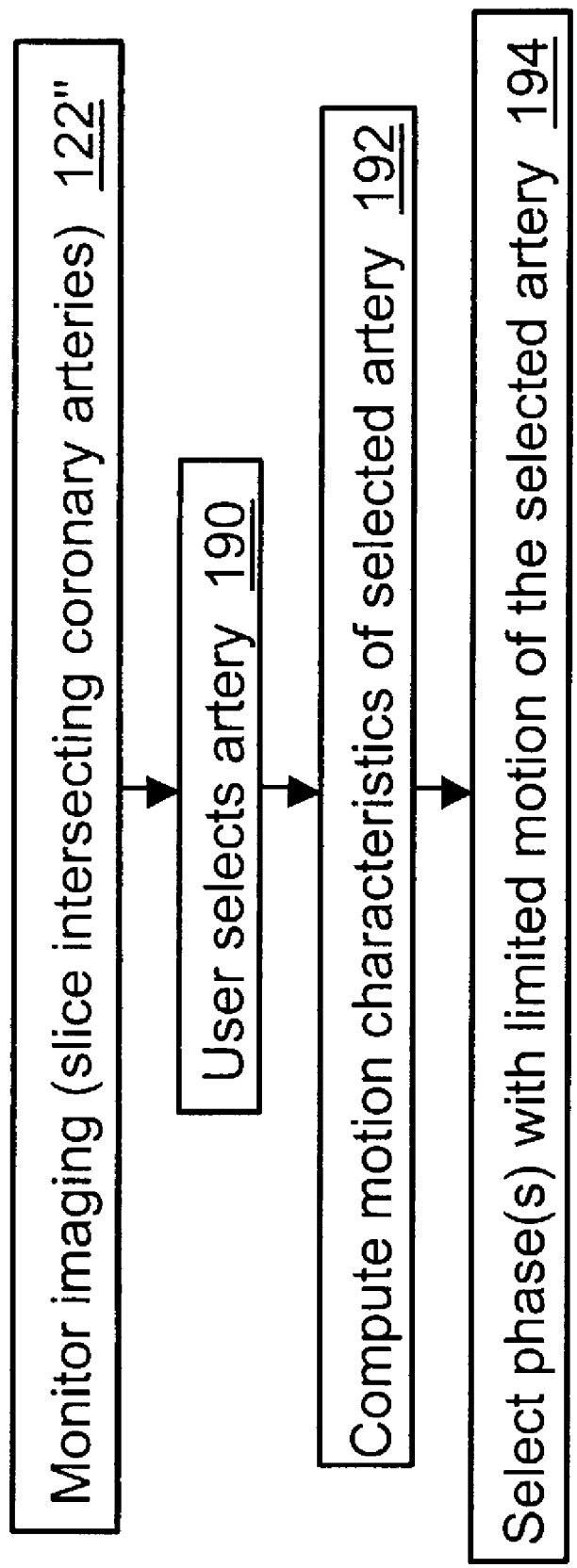
FIG. 5 shows another preferred embodiment for selecting optimal cardiac phases for a specific diagnostic objective as part of the preferred cardiac CT imaging session workflow.

With continuing reference to FIGS. 1 and 2 and with further reference to FIG. 5, a second preferred method for selecting a sub-set of the cardiac phases for high resolution reconstruction is described, which is particularly suitable for selecting cardiac phases optimized for coronary artery analysis. The rapid reconstruction step 122 performs a reconstruction of monitor images acquired in the step 108 and stored in the memory 32 in a step 122". For the phase selection method of FIG. 5, the monitor imaging 108 acquires axial slices that intersect one or more coronary arteries, in which the axial slices span at least one cardiac cycle period. Preferably, axial slices intersecting the three main coronary arteries feeding the heart are reconstructed in the step 122″ and stored in the phase selection images memory 54. One of the reconstructed axial images is displayed and the user selects an artery of interest in a step 190. Based on the images acquired during the step 122″ and corresponding electrocardiographic data, motion of the artery of interest over the cardiac cycle period is computed in a step 192, and one or more cardiac phases exhibiting limited motion of the selected artery are chosen as optimal phases in a step 194.

The rapid reconstruction and cardiac phase selection methods of FIGS. 4 and 5 are exemplary only. Other methods for performing rapid reconstruction using reduced voxel resolution or limited volume (e.g., slice) reconstruction can also be employed. The method for selecting optimal cardiac phases from the rapidly reconstructed images can be manual or automated, and is optionally tailored to the diagnostic objective 100, as for example the method 124″ is tailored to coronary artery analysis.

Figure 6:
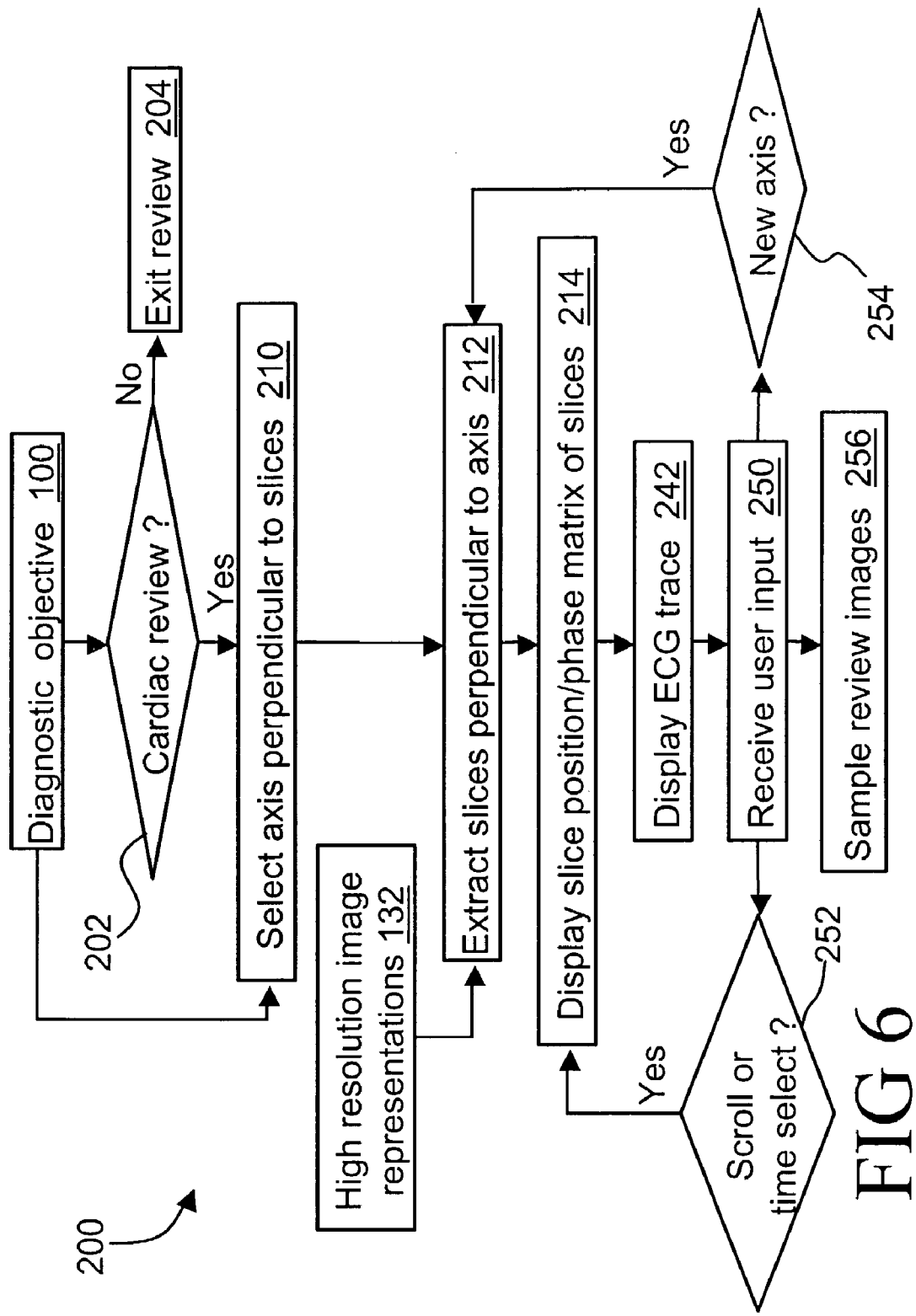
FIG. 6 shows a preferred method for performing a cardiac review component of the preferred workflow.

With continuing reference to FIGS. 1 and 2 and with further reference to FIG. 6, a preferred method 200 performed by the cardiac review processor 66 is described. Based on the diagnostic objective or objectives 100 a decision is made in a step 202 as to whether a cardiac review should be performed. If the diagnostic objective 100 is suitably accomplished without a manual review of the acquired image representations 132, the method 200 is exited in a step 204.

Assuming that cardiac review is deemed appropriate in the step 202, a three-dimensional orientation to be viewed is selected in a step 210. Typically, the selected orientation is the horizontal or vertical long axis, or a short axis, respective to a spatial orientation of the heart. However, an anatomical orientation (e.g., axial, sagittal, or coronal orientation) or other convenient orientation can be selected in the step 210. It will be appreciated that selecting the orientation in the step 210 is equivalent to selecting a planar orientation for the slices. Typically, this selection will be performed by the user from a drop-down list of axes or another interface. Optionally, the processor 60 selects the slice orientation based on the diagnostic objective 100. Moreover, it is contemplated to include icons or other selection elements by which the user can quickly select a slice orientation.

With the slice orientation effectively selected in the axis selection step 210, slices corresponding to the selected orientation are extracted from the three-dimensional high resolution reconstructed image representations 132 in a step 212. The extracted slices are displayed in a matrix or array format in a step 214.

Figure 7:
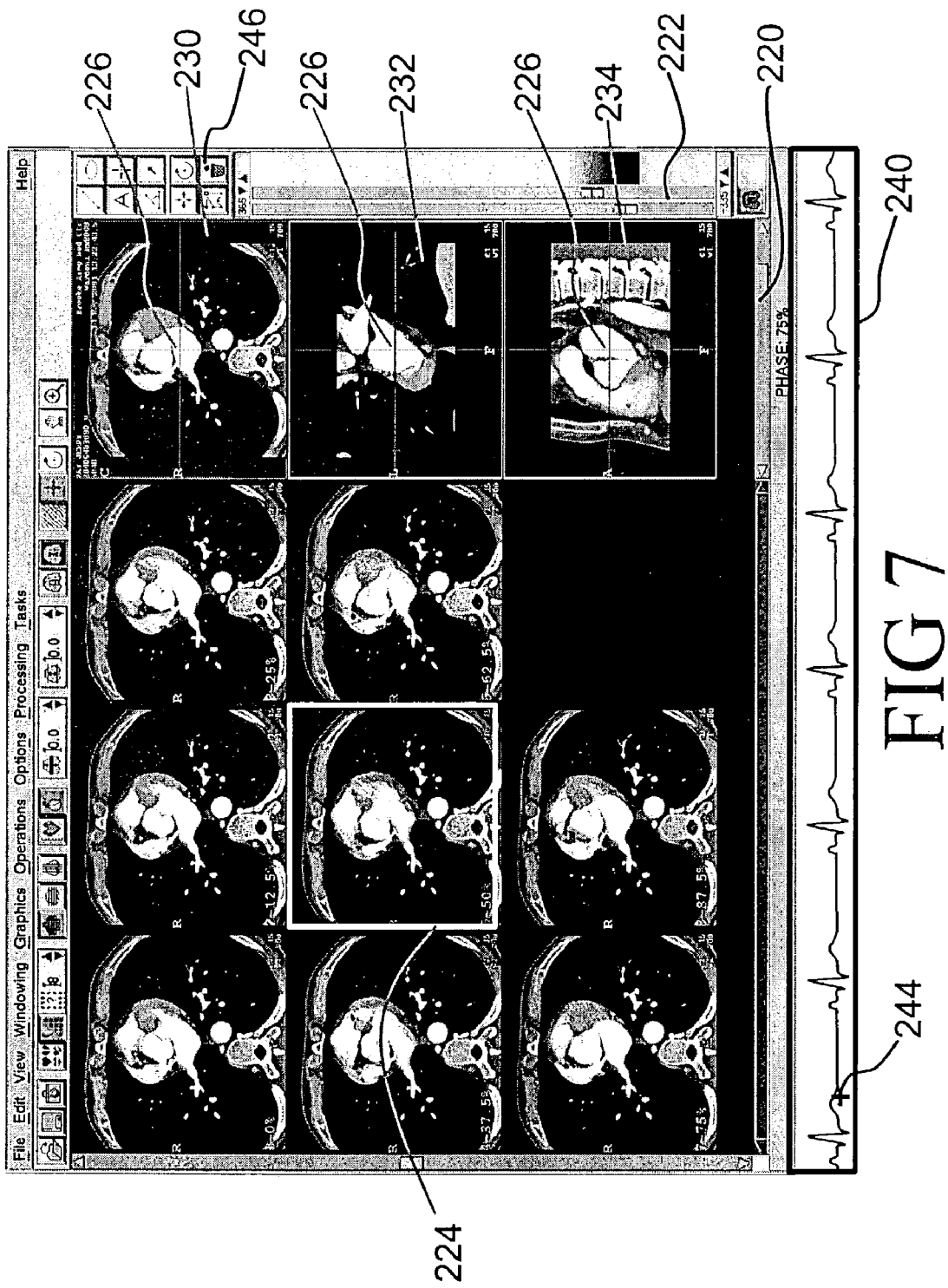
FIG. 7 shows an exemplary cardiac review display snapshot.

With continuing reference to FIGS. 1, 2, and 6, and with further reference to FIG. 7, the display step 214 preferably displays a matrix or array of image slices with one matrix axis (e.g., the horizontal axis in FIG. 7) indexing the cardiac phase and the orthogonal axis (e.g., the vertical axis in FIG. 7) indexing the slice. For a typical cardiac imaging session, over one thousand slices are acquired spanning a length of the heart and a full cardiac cycle period. Since this number of images is typically too large to view on a single display screen, the matrix display preferably includes horizontal and vertical scroll bars 220, 222 to enable the user to scroll through the slices.

A slice cursor 224 preferably identifies a currently selected slice. An image cursor 226 is provided for selecting a region of interest for visual enlargement or other processing. In the exemplary cardiac review display of FIG. 7, the image cursor 226 is displayed in an axial/coronal/sagittal tri-view including an axial slice 230, a coronal slice 232, and a sagittal slice 234, so that the cursor is spatially located in three dimensions. Alternatively, the slice views 230, 232, 234 are replaced by a three-dimensional rendering including the image cursor 226.

With continuing reference to FIGS. 1, 2, 6, and 7, an electrocardiographic (ECG) signal trace 240 acquired during the volumetric imaging 110 is displayed in a step 242. Preferably, the ECG trace 240 and the slices matrix are displayed simultaneously, such as is shown in FIG. 7. The ECG trace 240 preferably includes an ECG cursor 244 that indicates a location in the ECG trace substantially corresponding to the slice selected by the slice cursor 224. Preferably, the cursors 224, 226, 244 are linked; that is, movement of any one cursor by the user automatically updates the remaining cursors so that a spatial, cardiac phase, and temporal ECG correspondence is maintained between the cursors 224, 226, 244.

Optionally, a set of icons 246 is provided to perform rapid selections of certain common cardiac review parameters. For example, one of the icons 246 can select a viewing axis and initial cursor positions suitable for optimally viewing a selected coronary artery.

To move a cursor or perform other manipulations of the cardiac review, the user provides an input in a step 250 via the graphical user interface 46. The response of the cardiac review to the user input depends upon the type and value of the input 250. If the input 250 is recognized 252 as a scroll bar movement, the display is suitably updated in the step 214. If the input is recognized 254 as a change of the viewing axis, e.g. by user selection of a corresponding user icon 246, slices perpendicular to the new axis are extracted in the step 212 and displayed in the step 214. Preferably, prior to exiting the cardiac review, the user selects one or more exemplary review images 256, e.g. using the slice cursor 224, for later use in the report output 70.

The exemplary cardiac review display and method described above with particular reference to FIGS. 6 and 7 is readily modified by those skilled in the art to provide a convenient cardiac review for specific cardiac imaging applications. Optionally, the cardiac review display and method is adapted to a particular diagnostic objective 100. For example, the set of icons 246 can include icons for selecting optimal view parameters for one or more coronary arteries, with the coronary arteries icon or icons being displayed conditional upon the diagnostic objective 100 including an analysis of the coronary arteries.

Figure 8:
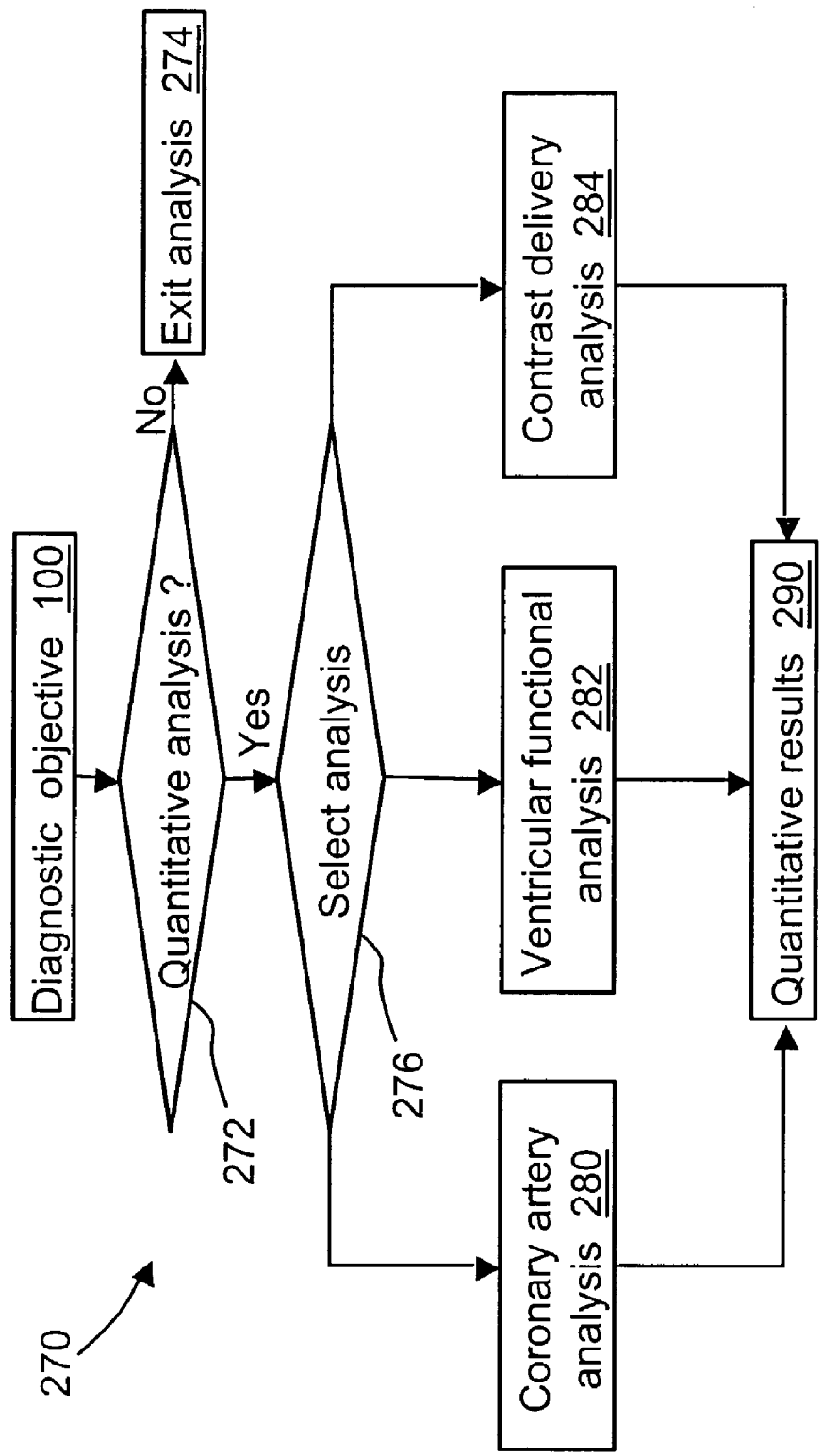
FIG. 8 shows a preferred method for selecting and implementing a quantitative cardiac CT analysis component of the preferred workflow.

With continuing reference to FIGS. 1 and 2 and with further reference to FIG. 8, a preferred method 270 implemented by the processor 60 for integrating quantitative analyses into the workflow is described. Based on the diagnostic objective or objectives 100 a decision is made in a step 272 as to whether one or more quantitative analyses should be performed. If the diagnostic objective 100 is suitably accomplished in a qualitative manner, for example by a qualitative cardiac review 200 to look for congenital cardiac defects, then the method 270 is exited in a step 274. If, however, one or more quantitative analyses is called for to accomplish the diagnostic objective 100, then a quantitative analysis is selected in a step 276, again based on the diagnostic objective 100. It will be appreciated that the selection steps 272, 276 are preferably automated based upon the diagnostic objective 100 and do not involve user input.

In the exemplary embodiment, three quantitative analyses are integrated into the cardiac workflow: coronary artery analysis 280; ventricular functional analysis 282; and contrast delivery analysis 284. Of course, additional and/or different quantitative analyses can also be integrated into the cardiac workflow. The selected quantitative analysis produces quantitative results or data 290 that are stored in the memory 62. It will be appreciated that a combination of two or three of the quantitative analyses 280, 282, 284 can be performed during a single cardiac CT session using a common set of imaging data, if such multiple quantitative analyses are called for by the diagnostic objective 100.

Figure 9:
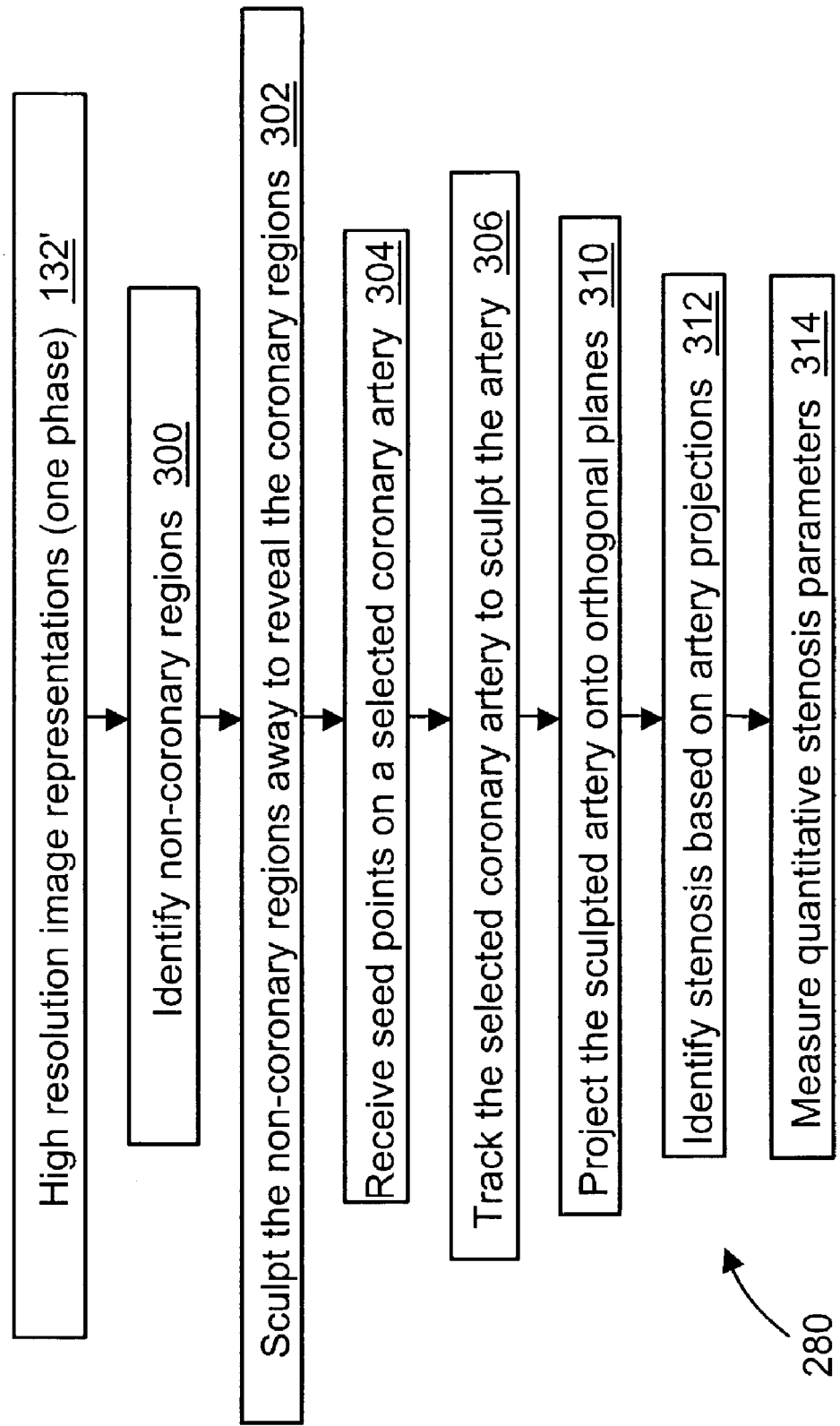
FIG. 9 shows a preferred method for performing the coronary artery analysis branch of the quantitative analysis component shown in FIG. 8.

With continuing reference to FIGS. 1, 2, and 8, and with further reference to FIG. 9, a preferred method for performing the coronary artery analysis 280 is described. For the coronary artery analysis 280, high resolution image representations 132' preferably correspond to a cardiac phase in which the coronary artery has limited motion. Such a cardiac phase is suitably selected by the local pathway of the cardiac phase selection method 124' (see FIG. 4) or by the cardiac phase selection method 124" (see FIG. 5). Non-coronary regions such as the lungs, spine, chest walls, and so forth are identified in a step 300, e.g. by user selection via a three-dimensional rendering, or by an automated process that identifies the non-coronary regions based on general anatomical considerations.

The identified non-coronary regions are sculpted away in a step 302 to reveal the coronary regions. The sculpting step 302 suitably employs a region growing technique based on tissue density to define the spatial extent of the identified non-coronary regions. The non-coronary regions are sculpted away by replacing the non-coronary voxels with zero-intensity voxels or by removing the non-coronary voxels from the image representation 132'.

With the non-coronary regions sculpted away, the coronary regions, i.e. the heart, the coronary arteries, and so forth, are revealed in the three-dimensional rendering. The user selects seed points corresponding to the coronary artery of interest in a step 304. The selected artery is tracked, e.g. using the region growing technique, and preferably sculpted out to create a coronary artery image representation in a step 306. The sculpted coronary artery is suitably displayed as a three-dimensional rendering, and/or is projected onto a projection plane in a step 310.

The projecting step 310 preferably projects maximum or minimum intensities along spatial curves corresponding to a centerline of the coronary artery to form a curvilinear MIP projection. Such an artery projection reflects a maximum or minimum extent of the vessel lumen along the tracked length. Hence, a stenosis or aneurysm of the coronary artery is evident in the MIP.

Any detected stenosis, aneurysm, or other vessel defect is identified from the artery projection in a step 312. Preferably, quantitative parameters of the stenosis are measured or otherwise extracted from the sculpted coronary artery or from renderings, MIP projections, or other representations thereof in a step 314. For example, quantitative parameters for designing a stent are optionally measured. In a preferred embodiment, quantitative analysis is facilitated by plotting the vessel lumen area or maximum diameter as a function of position along the tracked length. Stenoses and aneurysms are particularly evident in such a plot, and quantitative values for vessel narrowing or deformation are readily extracted from the quantitative vessel lumen plots.

Instead of identifying and sculpting away the non-coronary regions in the steps 300, 302, it is also contemplated to address the obscuring non-coronary tissues in other ways. For example, an axial/coronal/sagittal tri-view such as that shown in the cardiac review display of FIG. 7 in combination with a cursor similar to the image cursor 226 shown in FIG. 7 can be employed to allow the user to select the coronary artery seed points without prior sculpting removal of the non-coronary structures. However, selection via axial/coronal/sagittal tri-view requires substantial knowledge of anatomy as well as good three-dimensional visualization ability on the part of the user to avoid incorrect seed selections.

Figure 10:
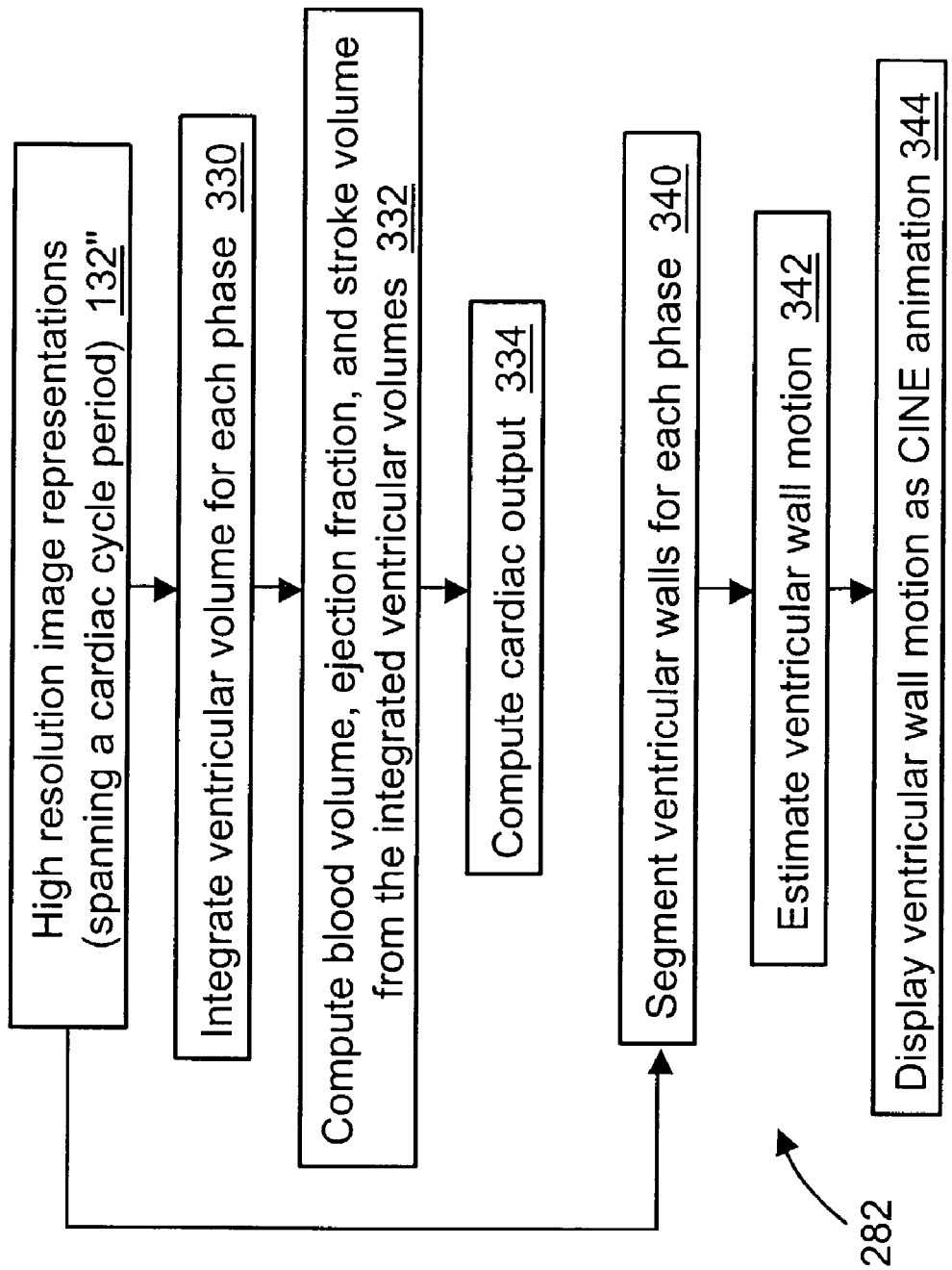
FIG. 10 shows a preferred method for performing the ventricular functional analysis branch of the quantitative analysis component shown in FIG. 8.

With continuing reference to FIGS. 1, 2, and 8, and with further reference to FIG. 10, a preferred method for performing the ventricular functional analysis 282 is described. For the ventricular functional analysis 282, high resolution image representations 132" preferably span a cardiac cycle period. Hence, all cardiac phases are preferably selected in the steps 120, 126 and reconstructed in the step 130. The ventricular volume is integrated for each cardiac phase in a step 330, for example by determining a spatial extent of the ventricular volume using region growing and summing the volume of the voxels comprising the ventricular volume.

The ventricular volumes of the several cardiac phases are compiled to form a plot of ventricular volume versus cardiac phase over the cardiac cycle period. Blood volume, ejection fraction, stroke volume, and/or similar quantitative parameters known in the art for characterizing ventricular function are computed from the ventricular volume-cardiac phase plot. By combining the ventricular volume performance computed in the step 332 with an average heart rate computed from the electrocardiographic data, the cardiac output is computed in a step 334.

In addition to the quantitative ventricular blood pumping performance computed in the steps 330, 332, 334, preferably the ventricular walls are defined or segmented for each cardiac phase in a step 340. The ventricular wall segmenting step 340 is optionally performed in conjunction with the volume-defining region growing of the step 330. The ventricular wall motion is estimated in a step 342, for example by measuring a Euclidean distance and speed of voxels corresponding to the ventricular wall over the cardiac cycle period. Optionally, the ventricular wall motion over the cardiac cycle period is displayed to the user as CINE animation in a step 344.

Figure 11:
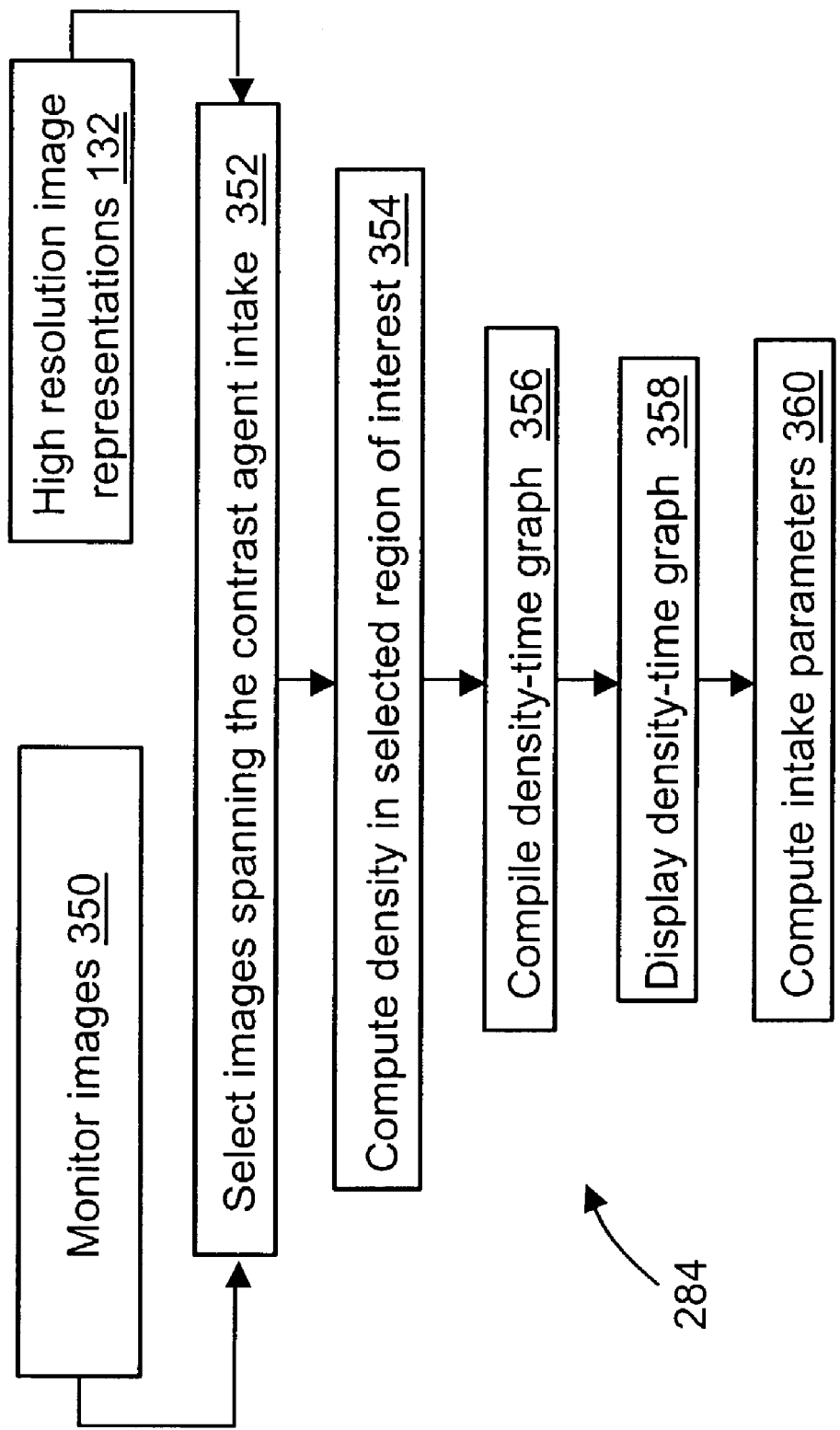
FIG. 11 shows a preferred method for performing the contrast delivery analysis branch of the quantitative analysis component shown in FIG. 8.

With continuing reference to FIGS. 1, 2, and 8, and with further reference to FIG. 11, a preferred method for performing the contrast delivery analysis 284 is described. Typically, the contrast delivery analysis 284 tracks intake of the contrast agent into the heart chambers and the coronary arteries and perfusion of the contrast agent into coronary tissues. With particular reference to FIG. 2, for contrast delivery analysis the contrast agent is administered to the patient in the step 106 as a rapid bolus injection. A substantial portion of the contrast agent intake occurs during the monitor imaging step 108, so that the high resolution image representations 132 reconstructed from imaging data acquired during the step 110 do not contain a substantial portion of the contrast agent intake interval.

Hence, the contrast delivery analysis 284 preferably accesses both the high resolution image representations 132 stored in the high resolution image representations memory 56 and monitor images 350 stored in the monitor images memory 52. Because the diagnostic objective which includes the contrast delivery analysis 284 is selected prior to the monitor imaging step 108, the imaging controller 40 optionally modifies the monitor imaging step 108 to ensure that adequate monitor images 350 are acquired during the monitoring 108. For volumetric contrast delivery analysis, the monitoring 108 is suitably interspersed with helical or multi-slice scans to provide volumetric monitor images 350.

For monitoring contrast agent intake in a small region of interest, a selected slice intersecting the region of interest is suitably acquired during the monitoring step 108. In particular, the region of interest for the contrast agent intake analysis 284 is preferably the same as the region of interest for the monitoring 108 shown in FIG. 3. In this case, the monitoring step 108 can be unmodified by inclusion of the contrast agent intake analysis 284 in the diagnostic objectives 100. However, if the monitoring step 108 typically employs relatively low resolution images, for contrast agent intake analysis 284 the monitoring step 108 can be modified to produce higher resolution monitor images 350.

Slices or volumetric images that substantially span the period of contrast agent uptake are selected in a step 352. These images are typically selected from both the monitor images 350 and the high resolution image representations 132 to span the contrast agent uptake time period. However, if the trigger condition of the monitoring step 108 is such that the contrast agent intake is substantially complete before the volume imaging 110 begins, the images selection step 352 optionally selects images solely from the monitor images 350.

For each selected image, a density of a selected region of interest is computed based on the voxel values in a step 354. The densities of the several selected images spanning the contrast agent intake period are compiled to generate a density-time graph in a step 356, which is preferably displayed to the user in a step 358. Contrast agent uptake parameters such as an exponential uptake time constant are computed in a step 360.

Rather than monitoring contrast agent intake, it is also contemplated to monitor removal of the contrast agent from the blood or from cardiac tissues over time. In this case, the images selection step 352 typically selects representative images from among the high resolution image representations 132. Because removal of the contrast agent from cardiac tissues typically occurs more slowly than uptake, the acquisition time for the high resolution imaging step 110 is preferably extended in response to a diagnostic objective 100 that includes monitoring contrast agent removal, and the rate of data acquisition is optionally slowed to reduce the total amount of data.

Figure 12:
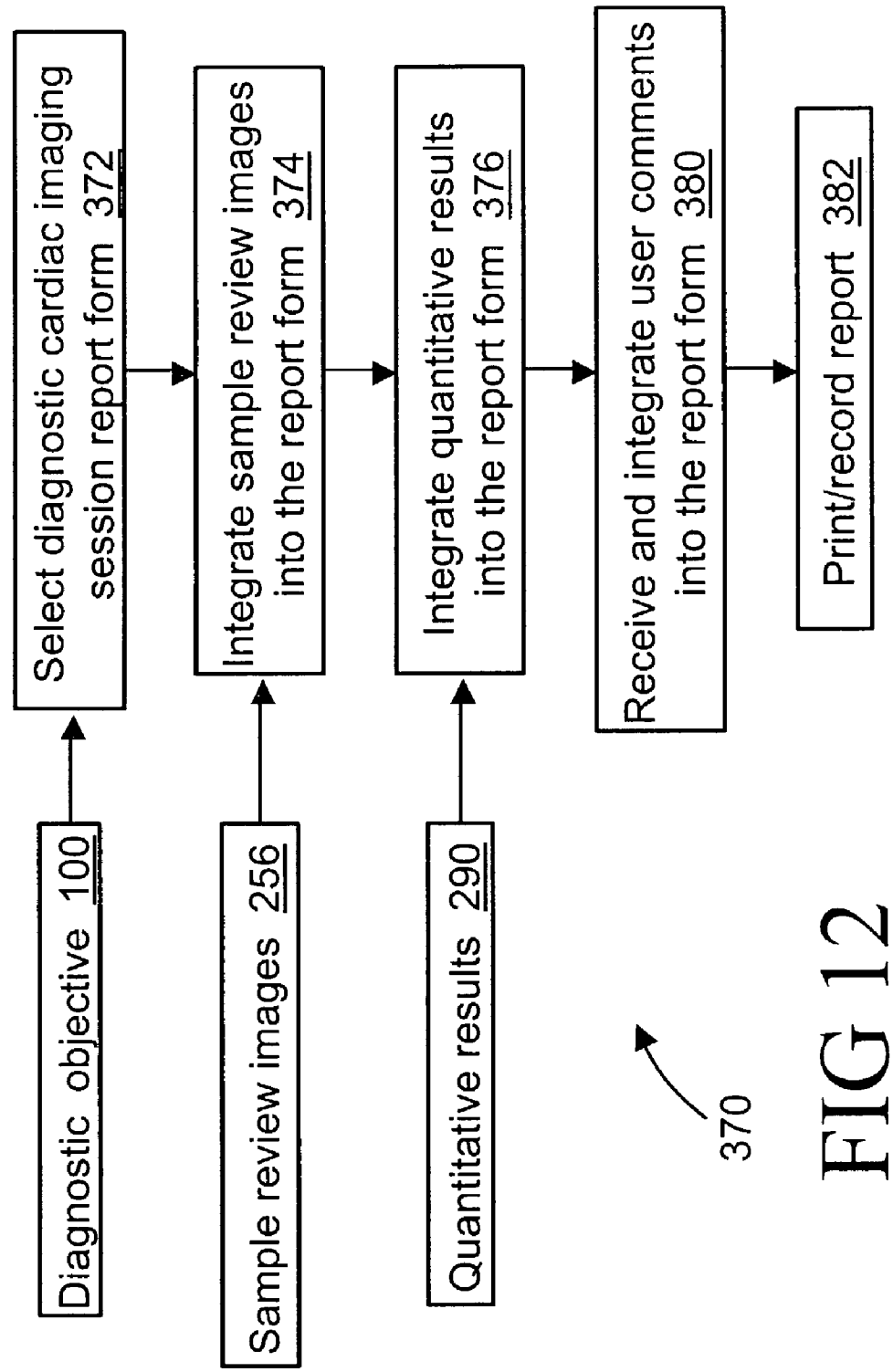
FIG. 12 shows a preferred method for constructing and outputting a cardiac CT session report as part of the preferred cardiac CT imaging session workflow.

With continuing reference to FIGS. 1 and 2 and with further reference to FIG. 12, a suitable method 370 for generating a cardiac CT imaging session report that efficiently combines qualitative and quantitative results is described. Based upon the diagnostic objective 100, a diagnostic cardiac CT imaging session report form is selected in a step 372. The report form is an electronic form including fields for receiving images, quantitative results, user comments, and the like, and is preferably specifically tailored to the diagnostic objective 100. In a step 374, sample images 256 selected during the cardiac review or other portions of the cardiac CT imaging session are integrated into the report form. The quantitative results 290 are similarly integrated into the report form in a step 376.

Of course, either of the steps 374, 376 are optionally omitted if the specific report form does not include fields for the corresponding information 256, 290. For example, in a cardiac CT imaging session performed to identify congenital heart defects, during which no quantitative analyses were performed, the step 376 is preferably omitted because: (i) there are no quantitative results 290; and (ii) the report form corresponding to the diagnostic objective 100 calling for qualitative cardiac review with no quantitative analyses does not include fields for quantitative results.

Preferably, the report form with the data 256, 290 integrated therein is displayed to the user and the user is prompted to input any appropriate additional comments in a step 380. A general comments field is suitably included in the report form for general user comments. Additionally, each sample image or quantitative result optionally includes a user comments input field so that a user comment pertaining to a particular sample image or quantitative result can be inputted and appears next to, under, or otherwise near the sample image or quantitative result.

The cardiac CT session report generated by integrating the data 256, 290 and additional user comments into the report form is preferably displayed, printed, electronically stored, magnetically stored, optically stored, electronically communicated, optically communicated, or otherwise processed in a step 382.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for performing a diagnostic cardiac imaging session of a patient's heart, the apparatus comprising:
   a monitor imaging means for monitor imaging a limited portion of the heart during influx of a contrast agent using a low patient x-ray exposure condition;
   a means for computing a contrast agent density corresponding to each monitor image for a region of interest;
   a means for computing and monitoring a time derivative of the contrast agent density based on temporally successive monitor images to detect a selected time derivative of the contrast agent density;
   a volume imaging means for volume imaging the heart to obtain volumetric imaging data, the volume imaging being initiated by a trigger that is based detection of the selected time derivative;
   a cardiac cycle recording means for recording cardiac cycle data during at least a portion of the imaging operations; and
   a volumetric reconstructing means for high resolution reconstructing at least a portion of the volumetric imaging data to produce high resolution image representations of at least a portion of the heart.

2. The apparatus as set forth in claim 1, further including:
   a cardiac phase selection means for selecting one or more optimal cardiac phases by rapidly reconstructing a portion of imaging data acquired during at least one of the monitor imaging and the volume imaging and selecting one or more optimal cardiac phases based on the rapidly reconstructed data and the cardiac cycle data that are optimal with respect to a diagnostic objective, wherein the volumetric reconstruction means reconstructs the optimal cardiac phases.

3. The apparatus as set forth in claim 2, wherein the monitor imaging means images a selected slice that intersects at least three main coronary arteries over at least one cardiac cycle of the heart, and the cardiac phase selection means includes:
   a means for computing a motion of a selected coronary artery based on the monitor images; and a means for identifying a cardiac phase for which the selected coronary artery has a low velocity based on the computed artery motion and corresponding cardiac cycle data.

4. The apparatus as set forth in claim 3, wherein the means for computing a motion of a selected coronary artery includes:
an edge-detection means for identifying edges of the selected coronary artery in each monitor image.

5. The apparatus as set forth in claim 2, wherein the cardiac phase selection means includes:
a low resolution reconstructing means for reconstructing volume images at a plurality of cardiac phases that span a cardiac cycle using a low voxel resolution; and
a means for selecting the one or more optimal cardiac phases based on the low voxel resolution volume images.

6. The apparatus as set forth in claim 5, wherein the means for selecting the one or more optimal cardiac phases includes:
an animation means for generating a CINE animation loop comprising the low voxel resolution volume images and for displaying the CINE animation loop.

7. The apparatus as set forth in claim 5, wherein the cardiac phase selection means further includes:
a reference reconstructing means for reconstructing a volume image at a reference cardiac phase using a high voxel resolution to generate a reference selection image;
a display means for displaying the reference selection image to a user for user selection of a region of interest therein; and
a means for computing a motion of the region of interest in the low voxel resolution volume images, the selecting means selecting one or more optimal cardiac phases in which the region of interest has limited motion.

8. The apparatus as set forth in claim 7, wherein a linear dimension ratio of the high voxel resolution to the low voxel resolution is 2:1, and a volume dimension ratio of the high voxel resolution to the low voxel resolution is 8:1.

9. The apparatus as set forth in claim 2, further including:
a processing means for performing a quantitative analysis on the reconstructed image representations corresponding to the optimal cardiac phases.

10. The apparatus as set forth in claim 9, wherein the processing means includes:
a ventricular functional analysis means for performing a ventricular functional analysis;
a contrast delivery analysis means for performing contrast delivery analysis;
a coronary artery analysis means for performing a coronary artery analysis; and
a selection means for selectively invoking at least one of the ventricular functional analysis means, the contrast delivery analysis means, and the coronary artery analysis means based on the diagnostic objective.

11. The apparatus as set forth in claim 9, wherein the volumetric reconstructing means produces volumetric images for a plurality of cardiac phases spanning at least a cardiac cycle period, the processing means including:
a means for integrating a ventricular volume for each cardiac phase of the plurality of cardiac phases; and
a means for computing a blood movement parameter of the ventricle for the cardiac cycle period based on the ventricular volumes of the plurality of cardiac phases.

12. The apparatus as set forth in claim 11, wherein the processing means further includes:

a means for segmenting voxels corresponding to ventricular walls for each of the plurality of cardiac phases; and
a means for estimating ventricular wall motion throughout the cardiac cycle period from the segmenting.

13. The apparatus as set forth in claim 9, wherein the volumetric reconstructing means produces a volumetric image for a selected cardiac phase in which the heart has limited motion, the processing means including:
a means for displaying a rendering of the high resolution volumetric image;
a means for identifying non-coronary regions including at least a sternum, a chest wall, and a spine in the high resolution volumetric image;
a sculpting means for removing the non-coronary regions from the rendering to expose coronary regions of interest;
an input means for receiving seed points on the sculpted rendering from a user, the seed points selecting a coronary vessel; and
a tracking means for tracking the selected coronary vessel starting from at least one seed point to sculpt out the selected coronary vessel.

14. The apparatus as set forth in claim 13, wherein the processing means further includes:
a means for projecting the sculpted coronary vessel onto a plurality of non-parallel planes to produce a plurality of projection views of the sculpted coronary vessel; and
a means for identifying a stenosis based on the projection views.

15. The apparatus as set forth in claim 1, further including:
a means for monitoring the cardiac cycle data during the volume imaging to detect an abnormal cardiac event, wherein the volume imaging means adjusts the volume imaging responsive to the abnormal cardiac event to reduce an effect of the abnormal cardiac event on the high resolution reconstructing.

16. The apparatus as set forth in claim 15, wherein the volume imaging means adjusts the volume imaging by discarding a portion of the volumetric imaging data that is acquired during the abnormal cardiac event, and interpolating volumetric imaging data to compensate for the discarded portion of the volumetric imaging data.

17. An apparatus for performing a diagnostic cardiac imaging session of a patient's heart, the apparatus comprising:
a survey imaging means for survey imaging the heart to determine optimized imaging parameter values for a received diagnostic objective;
a monitor imaging means for monitor imaging a limited portion of the heart during influx of a contrast agent using a low patient x-ray exposure condition to detect a trigger condition;
a volume imaging means for volume imaging the heart responsive to detection of the trigger condition using the optimized imaging parameter values to obtain volumetric imaging data;
a cardiac cycle recording means for recording cardiac cycle data during at least a portion of the survey imaging, the monitor imaging, and the volume imaging;
a volumetric reconstructing means for high resolution reconstructing the volumetric imaging data to produce high resolution image representations of at least a portion of the heart spanning a full cardiac cycle; and a cardiac review means for displaying a matrix of image slices of the high resolution image representations, the matrix including a horizontal axis indexing one of a spatial slice position and a cardiac phase, the matrix further including a vertical axis indexing the other of the spatial slice position and the cardiac phase, the displaying further including user-interactive horizontal and vertical scroll bars by which a user can scroll through the matrix of image slices.

18. The apparatus as set forth in claim 17, wherein the received diagnostic objective is selected from a group consisting of:
   a coronary artery analysis,
   a ventricular functional analysis,
   a contrast agent delivery analysis, and
   a qualitative visual cardiac review.

19. The apparatus as set forth in claim 17, wherein the cardiac cycle recording means includes:
   an electrocardiograph;
   a means for checking an electrocardiographic signal prior to the survey imaging; and
      a means for identifying a defective electrocardiograph lead connection based on the checking.

20. The apparatus as set forth in claim 17, wherein the imaging parameter values optimized by the survey imaging means include:
   a helical pitch for the volume imaging selected based on a cardiac cycle period extracted firm the cardiac cycle data and a survey image, and
   a dimension of the heart.

21. The apparatus as set forth in claim 17, wherein the cardiac cycle recording means includes an electrocardiograph, and the cardiac review means further includes:
   a means for displaying an electrocardiographic data graph together with the matrix of image slices, the electrocardiographic data graph including a graph cursor, wherein user selection of an image in the matrix causes the graph cursor to move to a corresponding electrocardiographic datum, and wherein user movement of the graph cursor to a selected electrocardiographic datum causes the matrix of image slices to include a corresponding image slice.

22. The apparatus as set forth in claim 17, wherein the cardiac review means further includes:
   a database of view parameter sets, each view parameter set being optimized for viewing a selected anatomical feature;
   wherein the displaying further includes a set of user selections corresponding to the view parameter sets, activation of a user selection by the user causing the matrix of image slices to be displayed using a selected one of the view parameter sets that corresponds to the activated user selection.

23. The apparatus as set forth in claim 17, further including:
   a report generating means for selecting one of a plurality of diagnostic cardiac imaging session report forms, the selected report form corresponding to the diagnostic objective, and for integrating at least one exemplary high resolution image representation into the selected report form.

24. A method for performing diagnostic cardiac imaging of a patient's heart using a computed tomography imaging scanner and a cardiac cycle monitor, the method comprising: acquiring images of a selected slice that intersects one or more coronary arteries over at least one cardiac cycle of the heart using a low patient x-ray exposure condition; computing a time derivative of a contrast agent density based on the coronary artery images; and based on the computed time derivative and corresponding cardiac cycle monitoring data, identifying a cardiac phase for which the selected coronary artery has a low velocity.

25. The method as set forth in claim 24, further including:
   detecting a trigger condition from the coronary artery images during influx of a contrast agent;
   volume imaging the heart responsive to detection of the trigger condition to obtain volumetric imaging data;
   recording cardiac cycle data during at least a portion of the imaging operations; and
   volumetric reconstructing at least a portion of the volumetric imaging data to produce high resolution image representations of at least a portion of the heart.

26. The method as set forth in claim 25, wherein the detecting of a trigger condition includes:
   detecting the trigger condition as a selected time derivative of the contrast agent density.

27. The method as set forth in claim 25, further including:
   displaying a matrix of slices of the high resolution image representations including a horizontal axis indexing one of a slice position and a cardiac phase and a vertical axis indexing the other of the slice position and the cardiac phase.

28. The method as set forth in claim 25, further including performing a quantitative analysis of the high resolution image representations, the quantitative analysis selected based upon a diagnostic objective from a group consisting of:
   a ventricular functional analysis,
   a contrast delivery analysis, and
   a coronary artery analysis.

* * * * *